United States Patent [19]
Oishi et al.

[11] Patent Number: 5,644,669
[45] Date of Patent: Jul. 1, 1997

[54] PHYSICAL PROPERTY EVALUATION METHOD FOR OPTICAL FIBER COATING, AND COATED OPTICAL FIBER

[75] Inventors: Kazumasa Oishi; Atsushi Suzuki; Nobuhiro Akasaka; Yasuo Matsuda, all of Yokohama, Japan

[73] Assignee: Sumitomo Electric Industries, Ltd., Osaka, Japan

[21] Appl. No.: 589,326

[22] Filed: Jan. 22, 1996

[30] Foreign Application Priority Data

Jan. 23, 1995 [JP] Japan ..................... 7-008202

[51] Int. Cl.⁶ .................................................. G02B 6/02
[52] U.S. Cl. .................................................. 385/123
[58] Field of Search ........................... 385/100, 122, 385/123, 128, 147; 428/368, 367, 439, 364, 391, 397, 400; 264/29.2, 1.28

[56] References Cited

U.S. PATENT DOCUMENTS

| | | | |
|---|---|---|---|
| 4,446,686 | 5/1984 | Panuska et al. | 385/100 |
| 4,671,950 | 6/1987 | Ogawa et al. | 423/447.1 |
| 4,782,129 | 11/1988 | Moschovis et al. | 428/378 |
| 4,794,133 | 12/1988 | Moschovis et al. | 524/99 |
| 5,277,973 | 1/1994 | Yamamura et al. | 428/367 |
| 5,403,660 | 4/1995 | Takabatake et al. | 428/367 |
| 5,510,185 | 4/1996 | Fujisawa et al. | 428/368 |

OTHER PUBLICATIONS

IEEE Communication Society Meeting 1995 "Modulus Measurement for Primary Coating of Dual–Coated Optical fiber" K. Mitsuhashi et al (no date) 1995.

"Solvent Swelling of Optical fiber coatings As A Diagnostic Measure of Crosslinking" P. Wiltzius et al. pp. 864–870 (no date) 1993.

"Push In Modulus Test For the Primary Coating of Dual––Coated Fiber", K. Oishi et al. pp. 552–558 (no date) 1994.

*Primary Examiner*—Akm E. Ullah
*Attorney, Agent, or Firm*—Lowe, Price, LeBlanc & Becker

[57] ABSTRACT

A physical property evaluation method for optical fiber coating which is easy in producing a sample and high in accuracy and which is capable of measuring the shear modulus or tensile modulus with high accuracy, and a coated optical fiber with good lateral pressure characteristics using this evaluation method. The method comprises a step of producing a sample with the both end faces being parallel by cutting a coated optical fiber by a plane normal to the direction of the center axis of an optically transparent member, a step of holding the sample by securing the second coating layer, a step of pushing only the optically transparent member to impose a load thereon, thereby giving displacement to the optically transparent member and causing shear elastic deformation to the first coating layer, and a step of calculating the shear modulus or tensile modulus of a material forming the first coating layer, based on an amount of the displacement of the optically transparent member and a value of the load imposed thereon.

5 Claims, 4 Drawing Sheets

PHYSICAL PROPERTY EVALUATION METHOD FOR OPTICAL FIBER COATING, AND COATED OPTICAL FIBER

BACKGROUND OF THE INVENTION

1. Field of the Invention

The present invention relates to a physical property evaluation method for optical fiber coating used in evaluation of a coating material in a coated optical fiber for optical transmission or in product inspection of coated optical fibers produced, and to the coated optical fiber.

2. Related Background Art

A coating of the coated optical fiber affects optical transmission characteristics or lateral pressure characteristics. Therefore, it is necessary to control physical properties, particularly, those of the first coating layer (primary layer).

A well known example of a method for evaluating the shear modulus of elasticity or the tensile modulus of elasticity of the first coating in the coated optical fiber is the one described in International Wire & Cable Symposium Proceedings 1993, p. 864. This evaluation method includes removing a part of the coating in the coated optical fiber, thereby producing a sample with only an optically transparent member or glass portion projecting, imposing a tensile load on the optically transparent member while securing the peripheral portion of the coated optical fiber, thereby causing shear elastic deformation to a material forming the first coating layer, thus measuring a shear modulus of elasticity of the material, and then converting it into a tensile modulus of elasticity.

SUMMARY OF THE INVENTION

It is an object of the present invention to provide a physical property evaluation method for the coating in the coated optical fiber, which is easy in producing a sample and high in accuracy and which permits the shear modulus and tensile modulus to be measured with high accuracy, and to provide a coated optical fiber with good lateral pressure characteristics by using the evaluation method.

The above object and other objects will be further apparent from the following description.

Provided according to the present invention is a method for evaluating a physical property of a first coating layer in a coated optical fiber having an optically transparent member, a first coating layer surrounding the periphery of the optically transparent member and being an elastic body, and a second coating layer surrounding the periphery of the first coating layer and having a higher tensile modulus of elasticity than the first coating layer has, which comprises: a step of producing a sample with the both end faces being parallel by cutting the coated optical fiber by a plane normal to a direction of the center axis of the optically transparent member; a step of holding the sample by fixing the second coating layer; a step of pushing only the optically transparent member to impose a load thereon, thereby giving displacement to the optically transparent member and causing shear elastic deformation to the first coating layer; and a step of calculating a shear modulus of elasticity or a tensile modulus of elasticity of the first coating layer, based on an amount of the displacement of the optically transparent member and a value of the load imposed thereon.

Also, it is preferred that a direction in which the load is imposed be the vertical direction.

Further, it is also possible that a plurality of the samples are arranged with the both end faces thereof being in accord so as to form a sample aggregate and the load is successively imposed on the plurality of the samples.

Also, provided according to the present invention is a coated optical fiber having the shear modulus of not more than 0.05 kg/mm$^2$, measured by the above method, or the tensile modulus of not more than 0.15 kg/mm$^2$.

In the present invention, the coated optical fiber is cut by the plane normal to the direction of the center axis of the optically transparent member in the coated optical fiber to produce the sample with the both end faces being parallel, the shear elastic deformation is caused to the first coating layer by pushing the optically transparent member to impose the load thereon while fixing the second coating layer, and the tensile modulus of the material forming the first coating layer is calculated based on a displacement amount and a value of the load imposed.

If a plurality of samples are bundled into a sample aggregate and the load is successively imposed on the samples, the tensile modulus of the first coating material can be continuously evaluated quickly and at high accuracy for the plurality of samples.

Further, a clear correlation is seen between the shear modulus or tensile modulus evaluated by the above evaluation method and the lateral pressure characteristics of the coated optical fiber. Accordingly, if the shear modulus or the tensile modulus is evaluated by the evaluation method, it becomes possible to estimate the lateral pressure characteristics of the coated optical fiber.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
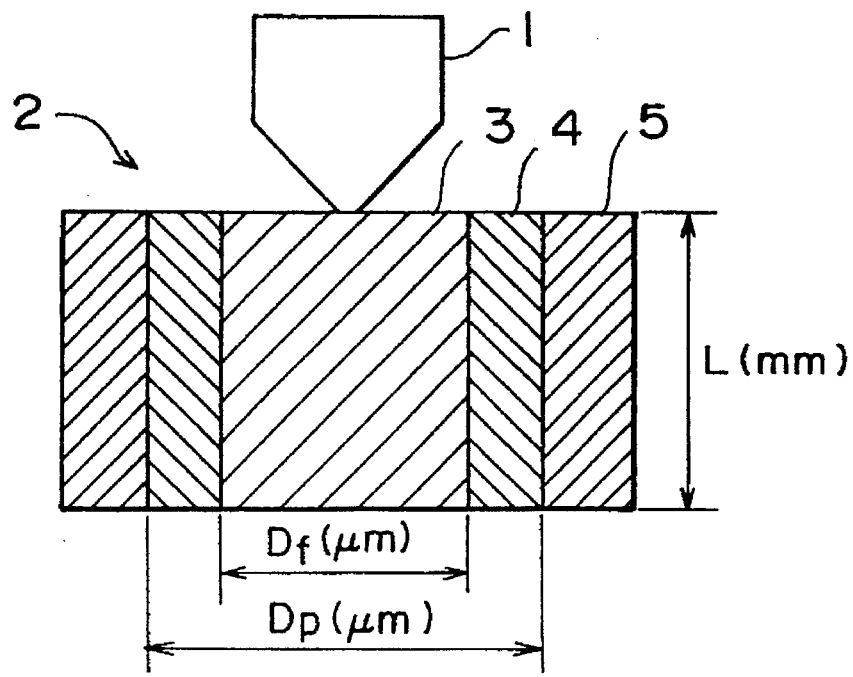
FIGS. 1 and 2 are explanatory drawings to show an embodiment of the physical property evaluation method for optical fiber coating arranged according to the present invention.

In the above-mentioned conventional technique, it is very difficult to produce the sample with high dimensional accuracy because the production of the sample according to the conventional evaluation method requires projecting only the optically transparent member while leaving the coating layer in specified dimensions. In other words, it is necessary to perform the processing of removing the coating layer by a cutting surface accurately normal to the center line of the coated optical fiber and good in flatness while leaving the optically transparent member in the center, which is very difficult. Even though the processing could be carried out, the dimensions would often differ sample from sample, resulting in dispersion in measurement results of the shear modulus and tensile modulus depending upon samples and degradation of the measurement accuracy.

On the other hand, a hardening state of the coating in the coated optical fiber greatly depends upon hardening conditions upon fiber drawing, and there is no correlation observed between the tensile modulus of a resin forming the first coating layer, evaluated in a sheet state, and the lateral pressure characteristics of the coated optical fiber formed by using the resin as a coating material. Therefore, in order to obtain coated optical fibers with good lateral pressure characteristics, it was necessary to evaluate the shear modulus and tensile modulus of the first coating layer in a fiber state and to clarify a correlation with the lateral pressure characteristics.

The embodiments of the present invention will be explained with reference to the accompanying drawings. In the drawings the same or correspondent portions will be denoted by the same reference numerals.

Figure 2:
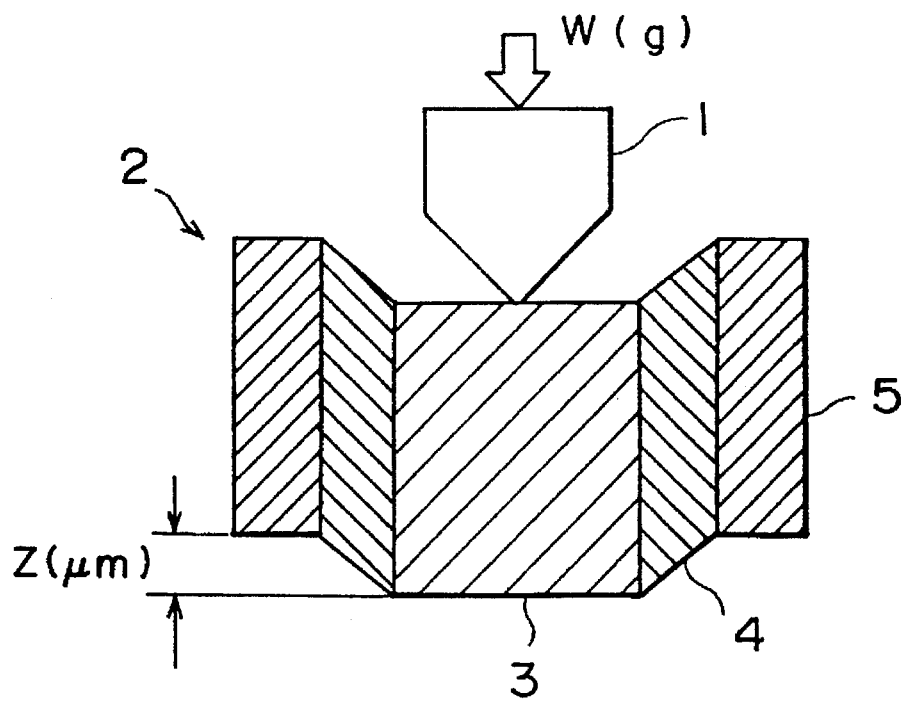

FIG. 1 and 2 are explanatory drawings to show the physical property evaluation method for optical fiber coating arranged according to the present invention, wherein FIG. 1 shows a state before the load is imposed on a sample 2 of the coated optical fiber by an indenter 1 and FIG. 2 shows a state while the load is imposed.

Here, the coated optical fiber has an optically transparent member 3 made of a glass in a circular cross section at the center thereof, a first coating layer (primary layer) 4 having a constant thickness surrounds the periphery of the optically transparent member 3, and a second coating layer (secondary layer) 5 having a constant thickness surrounds the periphery of the first coating layer 4. Normally, the first coating layer 4 is made of a flexible, elastic material, and the second coating layer 5 is made of a hard material that can be regarded as a rigid body.

The first coating layer 4 is made of the soft material, for example one selected from polymer materials such as ultraviolet-curing urethane acrylate resins (UV resins), and relatively soft materials such as silicone resins.

Further, the second coating layer 5 is made of the hard material having the tensile modulus of about 10 to 200 kg/mm$^2$ or about 50 to 180 kg/mm$^2$, for example one selected from polymer materials such as ultraviolet-curing urethane acrylate resins (UV resins) and ultraviolet-curing resins such as epoxy acrylate and ester acrylate.

The coated optical fiber thus formed is long, and a sample 2 with the both end faces being parallel and apart some mm is produced by cutting the coated optical fiber (polishing after slicing it) by a plane normal to the axial direction of the coated optical fiber, that is, normal to the direction of the center axis of the optically transparent member. Namely, the thickness of sample 2 is some mm. Since the processing of leaving the portion of the optically transparent member 3 as in the sample used in the conventional evaluation method is not required, the sample 2 can be readily produced and the dimensions thereof can be achieved with high accuracy.

Further, the chances that the end faces of the sample physically or chemically change are relatively remote as compared with the sample according to the conventional evaluation method.

After such a sample is produced, the peripheral portion of the hard second coating layer 5 is secured by a holding means not shown so as to hold the coated optical fiber 2, and in this state the indenter 1 of a dynamic ultra micro hardness tester or the like (not shown) pushes the optically transparent member 3 vertically downward to impose a load thereon, thereby giving displacement to the optically transparent member 3. Since the tip of the indenter 1 has a small area, it can apply the load accurately on the center of the optically transparent member 3. On this occasion, deformation of the second coating layer 5 is negligibly small, because the second coating layer 5 is made of the material that can be regarded as a rigid body as compared with the first coating layer 4. Because of this, shear elastic deformation occurs in the first coating layer 4, as shown in FIG. 2, by an amount of downward displacement of the optically transparent member 3.

The reason why the load is imposed in the vertical direction is that it can minimize influence of the gravity.

Here, supposing the thickness of sample 2, i.e. the gauge length, is L (mm), the diameter of the optically transparent member 3 is Df (μm), the outer diameter of the first coating layer 4 is Dp (μm), the load imposed is W (g), and the displacement amount of the optically transparent member 3 is Z (μm), the shear modulus of elasticity G (kg/mm$^2$) of the first coating layer 4 is expressed by the following conversion equation (1).

$$G=\{W/(2\pi LZ)\}\log_e(Dp/Df) \quad (1)$$

Here, supposing the Poisson's ratio of the first coating layer is v, the following relation of Equation (2) holds between the tensile modulus and the shear modulus. Here, the Poisson's ratio v can be assumed to be about 0.5.

$$E=2(1+v)G \quad (2)$$

Accordingly, the tensile modulus of elasticity E (kg/mm$^2$) of the first coating layer 4 is expressed by the following conversion equation (3).

$$E=\{(1+v)W/(\pi LZ)\}\log_e(Dp/Df) \quad (3)$$

Since the displacement amount and load value from the dynamic ultra micro hardness tester can be monitored as digital signals, extremely-high-accuracy measurement can be performed.

Figure 3:
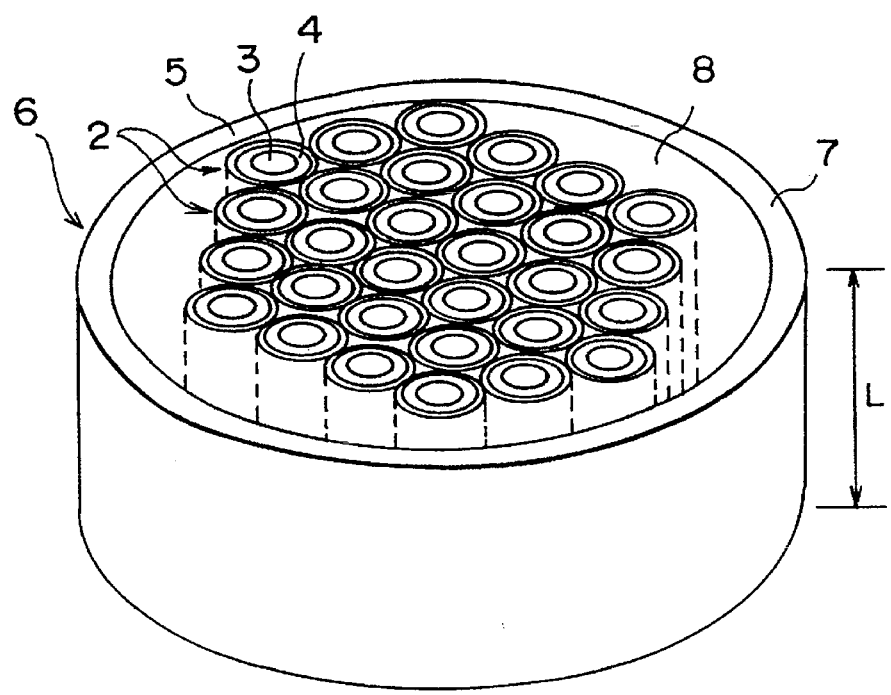
FIG. 3 is an explanatory drawing to show another embodiment of the physical property evaluation method for optical fiber coating arranged according to the present invention.

Another embodiment of the present invention is next explained based on FIG. 3. FIG. 3 shows a sample aggregate 6 including a plurality of samples 2 of coated optical fibers. This sample aggregate 6 is produced as follows.

First, coated optical fibers cut in the length of about 10 cm are put in an acrylic pipe 7 having the length of about 6 cm, the inner diameter of 4 mm, and the outer diameter of 8 mm, clearance is filled with an epoxy resin, and thereafter the epoxy resin is cured throughout about one day. After curing, the pipe 7 in which the coated optical fibers are inserted is cut into a length of L+α (where L is the above gauge length and α is a fine amount), and thereafter the both end faces thereof are polished. This polishing is carried out using a diamond liquid of 12 μmΦ.

This sample aggregate 6 does not require the processing of projecting only the portion of the optically transparent member 3 as in the sample used in the conventional evaluation method, and it has some size, specifically the diameter of 8 mm. Thus, it is readily produced. In addition, the individual samples 2 are simultaneously produced by production steps simultaneously carried out, and thus, characteristics of the all samples 2 become uniform. In FIG. 3, the epoxy resin 8 cured is present in the portions between the individual samples 2 and the pipe 7.

The side face of the sample aggregate 6 thus produced is pinched by a vise (not shown), and the indenter (not shown) of the dynamic ultra micro hardness tester successively (continuously) imposes the load rate of $1.1 \times 10^{-3}$ gf/s in order on the optically transparent members 3 in the individual samples 2. The successive imposition of the load rate is achieved by moving the sample aggregate 6 back and forth and right and left by an XY stage (not shown). Then displacement amounts of the optically transparent members 3 and load values this time are measured and stored. Based on the measurement values, the shear moduli G of the first coating layers 4 in the individual samples 2 are calculated by the conversion equation (1), and then the tensile moduli E of the first coating layers 4 in the individual samples 2 are calculated in order by the conversion equation (3).

Accordingly, data for the plurality of samples 2 can be obtained quickly. Further, because the individual samples 2 are uniform as described above, the dispersion in the tensile moduli E of the first coating layers 4 thus obtained for the individual samples 2 becomes small, and thus, high-accuracy measurement becomes possible.

Figure 4:
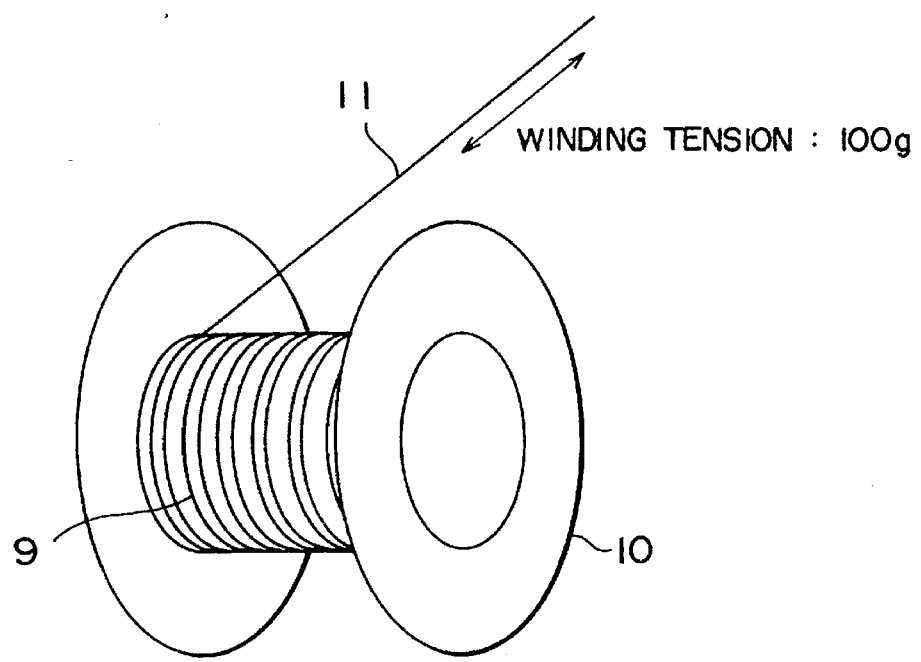
FIG. 4 is a perspective view to show a state in which lateral pressure against bobbin is being measured

Another embodiment is next explained referring to FIG. 4 to FIG. 7. As shown in FIG. 4, the coated optical fiber 11 is wound in one layer around a bobbin 10 in which a sand paper 9 of #1000 according to JIS is stuck on a cylinder portion. A winding tension this time is set to 100 g. The outer diameter of the cylinder portion of the bobbin 10 is 28 cm. The length of the coated optical fiber 11 thus wound around the bobbin 10 is about 500 m. An optical transmission loss L3 per 1 km at the wavelength 1.55 m, of this coated optical fiber 11 is measured by the cut back method within 30 minutes immediately after winding.

Figure 5:
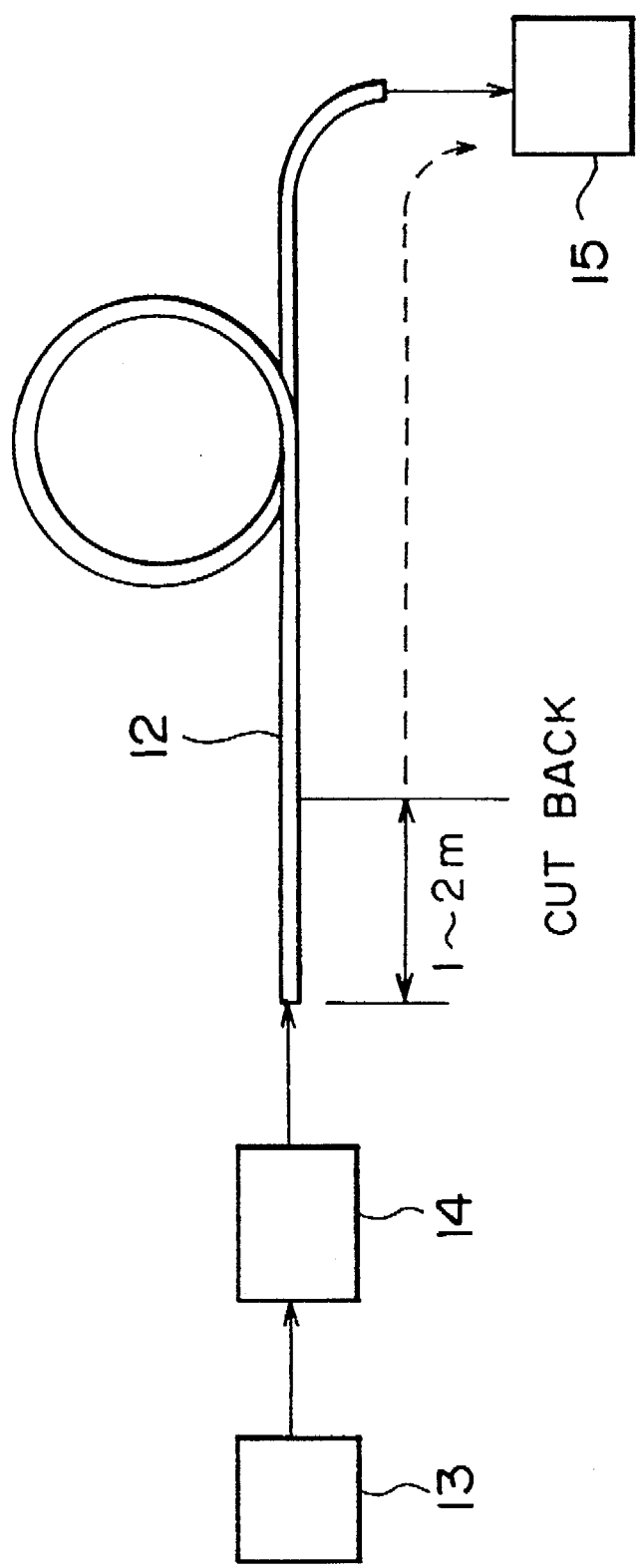
FIG. 5 is a perspective view to illustrate the cut back method.

Here, the cut back method is one of methods for measuring the optical loss. The cut back method is explained below. As shown in FIG. 5, light is guided from a light source 13 and through an incidence optical system 14 into an optical fiber 12, and power P1 ($\lambda$) of transmitted light is measured by a photosensor 15. Next, the optical fiber 12 is cut at 1 to 2 m from the entrance end and light power P0 ($\lambda$) is similarly measured. This procedure is why it is called as cut back. From the two measurements, a loss $\alpha(\lambda)$ is calculated by the following equation (4).

$$\alpha(\lambda) = -10 \log (P1(\lambda)/P0(\lambda))[dB] \quad (4)$$

The details of the cut back method can be found for example on pp (3–15) to (3–16), Katsuhiko OKUBO, "Optical Fiber Technology in ISDN era," Rikogakusha (1989). In the measurements by the cut back method in the present embodiment, FML-100 wavelength loss meter (including power meter) manufactured by Operex Co. was used as a spectrometer.

Separately from such measurement of optical transmission loss L3, another optical transmission loss L4 per 1 km at the wavelength 1.55 μm is measured by the cut back method in a bundle state of the same optical fiber in the length of 1000 m, that is, in a state where the optical fiber is not wound around a bobbin or the like.

Subtracting the optical transmission loss L4 in the bundle state from the optical transmission loss L3 in the wound state thus measured, a difference (L3–L4) between them is defined as a loss increment. The loss increment is one of the lateral pressure characteristics. For the coated optical fiber, the loss increment of the optical transmission loss at wavelength 1.55 μm is preferably not more than 1.0 dB/km.

Table 1 given below shows a correlation between the lateral pressure characteristic (loss increment) against bobbin 10 and the shear modulus of the first coating layer 4 and similarly a correlation between the lateral pressure characteristic (loss increment) and the tensile modulus of the first coating layer 4. The left end column in Table 1 shows tensile moduli of the first coating layer 4 by sheet (in a sheet state).

[Table 1]

Correlations between lateral pressure characteristic against bobbin and shear and tensile moduli of first coating layer (wavelength 1.55 μm)

| Tensile modulus by sheet (kg/mm²) | Obtained for first coating layer in fiber state by the method according to the invention | | Lateral pressure characteristic loss increment (dB/km) |
|---|---|---|---|
| | Shear modulus (kg/mm²) | Tensile modulus (kg/mm²) | |
| 0.30 | 0.045 | 0.13 | 0.86 |
| | 0.062 | 0.18 | 1.60 |
| | 0.103 | 0.30 | 2.61 |
| 0.20 | 0.034 | 0.10 | 0.71 |
| | 0.055 | 0.16 | 1.10 |
| | 0.069 | 0.20 | 2.06 |
| 0.15 | 0.028 | 0.08 | 0.53 |
| | 0.034 | 0.10 | 0.71 |
| | 0.052 | 0.15 | 0.94 |
| 0.10 | 0.021 | 0.06 | 0.45 |
| | 0.034 | 0.10 | 0.71 |
| 0.05 | 0.017 | 0.05 | 0.42 |

As shown in this Table 1, little correlation is seen between the tensile modulus by sheet and the lateral pressure characteristic against bobbin. For example, when the tensile modulus by sheet is constant at 0.30 kg/mm², the loss increment changes more than three times from 0.86 dB/km to 2.61 dB/km; further, when the tensile modulus by sheet is constant at 0.20 kg/mm², the loss increment changes about three times from 0.71 dB/km to 2.06 dB/km. Therefore, it is almost impossible to determine the value of lateral pressure characteristic against bobbin from the value of tensile modulus by sheet.

Figure 6:
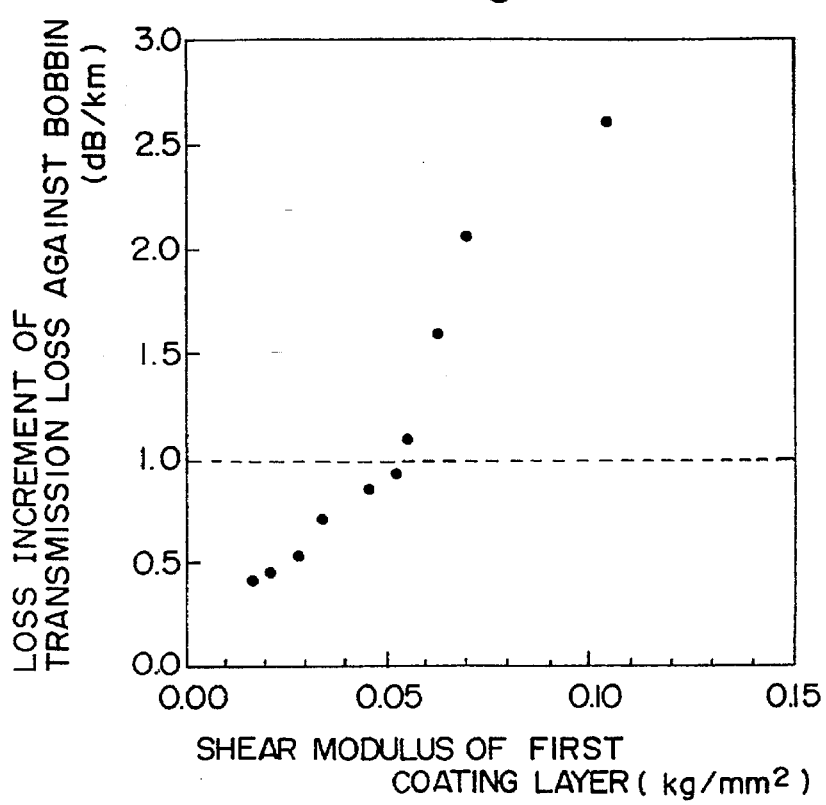
FIG. 6 is a graph to show a relation between the shear modulus of the first coating layer and the loss increment of the transmission loss against bobbin.

In contrast, a correlation as shown in FIG. 6 exists between the shear modulus of the first coating layer 4 measured by the method of the above embodiment (namely, the shear modulus obtained by producing a sample with the both end faces being parallel by cutting the coated optical fiber by a plane normal to the direction of the center axis of the optically transparent member, arranging a plurality of samples with the both end faces thereof being in accord so as to form a sample aggregate, holding the sample aggregate to fix the second coating layers in the samples enclosed in the sample aggregate, pushing the optically transparent members for the plurality of samples to continuously impose the load thereon, thereby giving displacement to the optically transparent members and causing shear elastic deformation to the first coating layers, and further calculating the shear modulus of the first coating layer, based on displacement amounts of the optically transparent members and load values imposed thereon) and the loss increment of the transmission loss against bobbin at wavelength 1.55 μm. Accordingly, the loss increment of the transmission loss against bobbin can be estimated from the shear modulus measured by the above method.

Figure 7:
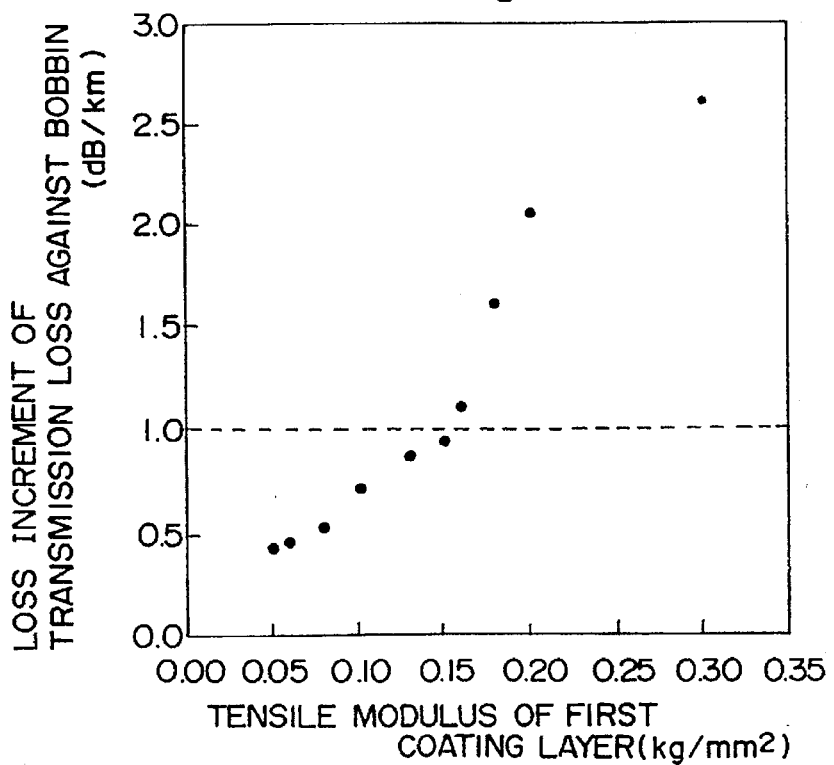
FIG. 7 is a graph to show a relation between the tensile modulus of the first coating layer and the loss increment of the transmission loss against bobbin.

Similarly, a correlation as shown in FIG. 7 exists between the tensile modulus of the first coating layer 4 measured by the method of the above embodiment and the loss increment of the transmission loss against bobbin at wavelength 1.55 μm. Accordingly, the loss increment of the transmission loss against bobbin can be estimated from the tensile modulus measured in this manner.

As described previously, the loss increment of the optical transmission loss at wavelength 1.55 μm is preferably not more than 1.0 dB/km. This line of 1.0 dB/km is illustrated by a dotted line in FIG. 6 and FIG. 7. Thus, from FIG. 6, the shear modulus of the first coating layer 4 is preferably not more than about 0.05 kg/mm². Further, from FIG. 7, the tensile modulus of the first coating layer 4 is preferably not more than about 0.15 kg/mm². As described, when the shear modulus of the first coating layer 4 is evaluated by the above method, and if the shear modulus thereof is not more than 0.05 kg/mm², the loss increment of the coated optical fiber can be estimated to be not more than 1.0 dB/km. Similarly, when the tensile modulus of the first coating layer 4 is evaluated by the above method, and if the tensile modulus is not more than 0.15 kg/mm², the loss increment of the coated optical fiber can be estimated to be not more than 1.0 dB/km.

As explained above, the present invention involves the step of producing the sample with the parallel both end faces by cutting the coated optical fiber by the plane normal to the direction of the center axis of the optically transparent member, the step of holding the sample by securing the second coating layer, the step of pushing only the optically transparent member to impose the load thereon, thereby giving displacement to the optically transparent member and causing shear elastic deformation to the first coating layer, and the step of calculating the shear modulus and tensile modulus of the first coating layer, based on displacement amounts of the optically transparent members and values of the loads imposed thereon, which permits the sample to be produced easily and at high accuracy and which can realize the physical property evaluation method for optical fiber coating capable of measuring the shear modulus and tensile modulus of the first coating layer at high accuracy.

When a plurality of samples are arranged with the both end faces thereof being in accord so as to form a sample aggregate and the load is successively imposed on the plurality of samples, many uniform samples can be produced and the shear moduli and tensile moduli of the plural samples can be measured quickly.

Further, if the shear modulus and tensile modulus of the first coating layer are evaluated by the physical property evaluation method for optical fiber coating as described and if a coated optical fiber is provided so that the shear modulus is not more than 0.05 kg/mm² or so that the tensile modulus is not more than 0.15 kg/mm², this coated optical fiber will have good lateral pressure characteristics.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims. The basic Japanese Applications No.69534/1994 filed on Apr. 7, 1994 and No.8202/1995 filed on Jan. 23, 1995 are hereby incorporated by reference.

What is claimed is:

1. A method for evaluating a physical property of a first coating layer in a coated optical fiber having an optically transparent member, the first coating layer surrounding the periphery of the optically transparent member and being an elastic body, and a second coating layer surrounding the periphery of the first coating layer and having a higher tensile modulus of elasticity than said first coating layer has, which is a physical property evaluation method for optical fiber coating, comprising:

a step of producing a sample with the both end faces being parallel by cutting said coated optical fiber by a plane normal to a direction of the center axis of said optically transparent member;

a step of holding said sample by fixing said second coating layer;

a step of pushing only said optically transparent member to impose a load thereon, thereby giving displacement to said optically transparent member and causing shear elastic deformation to said first coating layer; and a step of calculating a shear modulus of elasticity or a tensile modulus of elasticity of said first coating layer, based on an amount of the displacement of said optically transparent member and a value of the load imposed thereon.

2. A method according to claim 1, wherein a direction in which said load is imposed is the vertical direction.

3. A method according to claim 1, wherein a plurality of said samples are arranged with the both end faces thereof being in accord so as to form a sample aggregate and said load is successively imposed on the plurality of said samples.

4. A coated optical fiber comprising an optically transparent member, a first coating layer surrounding the periphery of the optically transparent member and being an elastic body, and a second coating layer surrounding the periphery of the first coating layer and having a higher tensile modulus of elasticity than said first coating layer has, which is a coated optical fiber characterized in that:

a shear modulus of elasticity of said first coating layer is not more than 0.05 kg/mm² when calculated in such a manner that a sample with the both end faces being parallel is produced by cutting said coated optical fiber by a plane normal to a direction of the center axis of said optically transparent member, a plurality of said samples are arranged with the both end faces thereof being in accord so as to form a sample aggregate, said sample aggregate is held to fix said second coating layers of said samples enclosed in said sample aggregate, a load is successively imposed on the plurality of said samples by pushing said optically transparent members, thereby giving displacement to said optically transparent members and causing shear elastic deformation to said first coating layers, and the shear modulus of elasticity of said first coating layer is calculated based on amounts of the displacement of said optically transparent members and values of the load imposed thereon.

5. A coated optical fiber comprising an optically transparent member, a first coating layer surrounding the periphery of the optically transparent member and being an elastic body, and a second coating layer surrounding the periphery of the first coating layer and having a higher tensile modulus of elasticity than said first coating layer has, which is a coated optical fiber characterized in that:

a tensile modulus of elasticity of said first coating layer is not more than 0.15 kg/mm² when calculated in such a manner that a sample with the both end faces being parallel is produced by cutting said coated optical fiber by a plane normal to a direction of the center axis of said optically transparent member, a plurality of said samples are arranged with the both end faces thereof being in accord so as to form a sample aggregate, said sample aggregate is held to fix said second coating layers of said samples enclosed in said sample aggregate, a load is successively imposed on the plurality of said samples by pushing said optically transparent members, thereby giving displacement to said optically transparent members and causing shear elastic deformation to said first coating layers, and the tensile modulus of elasticity of said first coating layer is calculated based on amounts of the displacement of said optically transparent members and values of the load imposed thereon.

* * * * *